United States Patent [19]
Norgard

[11] Patent Number: 4,868,118
[45] Date of Patent: Sep. 19, 1989

[54] CLONING AND EXPRESSION OF THE 47-KILODALTON ANTIGEN OF TREPONEMA PALLIDUM

[75] Inventor: Michael V. Norgard, Plano, Tex.

[73] Assignee: Board of Regents, The University of Texas System, Austin, Tex.

[21] Appl. No.: 913,724

[22] Filed: Sep. 30, 1986

[51] Int. Cl.[4] .................. C12N 1/20; C12N 15/00; C12R 1/185

[52] U.S. Cl. .................. 435/252.33; 435/320; 435/68; 530/350; 424/88

[58] Field of Search .................. 435/68, 172.3, 172.2, 435/320, 253, 252.3, 252.33

[56] References Cited

U.S. PATENT DOCUMENTS 4,514,498  4/1985  Kettman et al. .................. 435/240

FOREIGN PATENT DOCUMENTS

WO 84/01961  5/1984  Int'l Pat. Institute.
PCT/US83/-
01718  5/1984  World Int. Prop. O..

OTHER PUBLICATIONS

Alderete and Baseman, Infect. Immun., 30:814–823, 1980.
Baker-Zander and Lukehart, Infect. Immun., 42:634–638, 1983.
Baker-Zander and Lukehart, Infect. Immun., 46:116–121, 1984.
Baker-Zander et al., J. Infect. Dis., 151:264–272, 1985.
Bishop and Miller, J. Immunol., 117:197–207, 1976.
Coates et al., Abst. 85th Ann. Mtg. Amer. Soc. Microbiol., 1985, Abstract #C-29, p. 304.
Fehniger et al., Infect. Immun., 46:598–607, 1984.
Fehniger et al., Abst. 85th Ann. Mtg. Amer. Soc. Microbiol., 1985, Abstract #B-156, p. 44.
Hanff et al., J. Immunol., 129:1287–1291, 1982.
Hansen et al., J. Bacteriol, 162:1227–1237, 1985.
Hook et al., J. Clin. Microbiol., 22:241–244, 1985.
Jones et al., J. Exp. Med., 160:1404–1420, 1984.
Lukehart et al., J. Immunol., 129:833–838, 1982.
Lukehart et al., J. Immunol., 134:585–592, 1985.
Lukehart et al., Sex. Trans. Dis., Jan.–Mar., 1986, pp. 9–15.
Marchitto et al., Infect. Immun., 45:660–666, 1984.
Moseley et al., J. Infect. Dis., 142:892–898, 1980.
Moskophidis and Muller, Infect. Immun., 43:127–132, 1984.

(List continued on next page.)

*Primary Examiner*—Blondel Hazel
*Attorney, Agent, or Firm*—Arnold, White & Durkee

[57] ABSTRACT

Monoclonal antibodies directed against the 47 kDa major outer membrane surface immunogen of virulent *Treponema pallidum* were used to select *E. coli* recombinant clones expressing the 47 kDa immunogen. The phenotype of the clones was dependent on the presence of recombinant plasmid in the host cell. Southern hybridization revealed that the cloned *T. pallidum* DNA sequence was an accurate representation of the *T. pallidum* genomic DNA arrangement. Purified IgG from rabbits experimentally infected with *T. pallidum* and human secondary syphilitic sera specifically reacted with the clones while normal human serum or IgG from normal rabbit serum did not. Results of Southern hybridization indicated that a homologous 47 kDa immunogen gene was absent in at least 4 species of nonpathogenic treponemes tested, as well as from total rabbit genomic DNA. Rabbit anti-*T. phagedenis* biotype Reiter (treponemal nonpathogen) antiserum and a monoclonal antibody directed against a "common" treponemal determinant were unreactive with the clones. Western blotting and radioimmunoprecipitation experiments with specific monoclonal antibodies revealed that the recombinant (*E. coli*) and native (*T. pallidum*) forms of the antigen had identical electrophoretic mobilities. The availability of recombinant 47 kDa immunogen provides a new opportunity for biochemical analysis of the protein, structure-function studies, examination of its role in microbial pathogenesis, and assessment of its diagnostic and vaccinogenic potentials.

4 Claims, 5 Drawing Sheets

OTHER PUBLICATIONS

Norgard, Anal. Biochem., 113:34–42, 1981.
Norgard and Miller, Science, 213:553–555, 1981.
Norgard and Miller, Infect. Immun., 42:435–445, 1983.
Norgard et al., J. Clin. Microbiol, 20:711–717, 1984.
Norris and Sell, J. Immuno., 133:2686–2692, 1984.
Penn et al., J. Gen. Microbiol., 131:2349–2357, 1985.
Robertson et al., Infect. Immun., 36:1076–1085, 1982.
Rodgers et al., Abst. 85th Ann. Mtg. Amer. Soc. Microbiol., 1985, Abstract #C-30, p. 305.
Stamm et al., Infect. Immun., 36:1238–1241, 1982.
Stamm et al., Infect. Immun., 41:709–721, 1983.
Strugnell et al., Infect. Immun., 51:957–960, 1986.
Thornburg and Baseman, Infect. Immun., 42:623–627, 1983.
Thornburg et al., Genitourin. Med., 61:1–6, 1985.
Van De Donk et al., Develop. Biol. Standard., 57:107–111, 1984.
Van Eijk and Van Embden, Antonie van Leeuwenhoek, 48:486–487, 1982.
Van Embden et al., Infect. Immun., 42:187–196, 1983.
Van De Donk et al., Innovations and Biotechnology, 1984.
Walfield et al., Science, 216:522–523.
Marchitto et al. (1986), Infection and Immunity, 51:168–176.
Norgard et al., (1986), Infection and Immunity, 54:500–506.
Peterson et al., (1986), J. Exp. Med., 164:1160–1170.
Swancutt et al., (1986), Infection and Immunity, 52:110–119.
Marchitto, Kevin S., Monoclonal Antibody Analysis of Specific Antigenic Similarities Among Pathogenic Treponema Pallidum Subspecies, Infection and Immunity, Sep. 1984, pp. 660–666.
PCT International Search Report for PCT International Appln. No. PCT/US87/02403.
Swancutt, M. et al., Monoclonal Antibody Selection and Analysis of a Recombinant DNA-Derived Surface Immunogen of Treponema Pallidum Expressed in Escherichia coli, Infection and Immunity, Apr. 1986, pp. 110–119.
Norgard, M. V. et al., Cloning and Expression of the Major 47-Kilodalton Surface Immungen of Treponema Pallidum in *Escherichia coli*, Infection and Immunity, Nov. 1986, pp. 500–506.

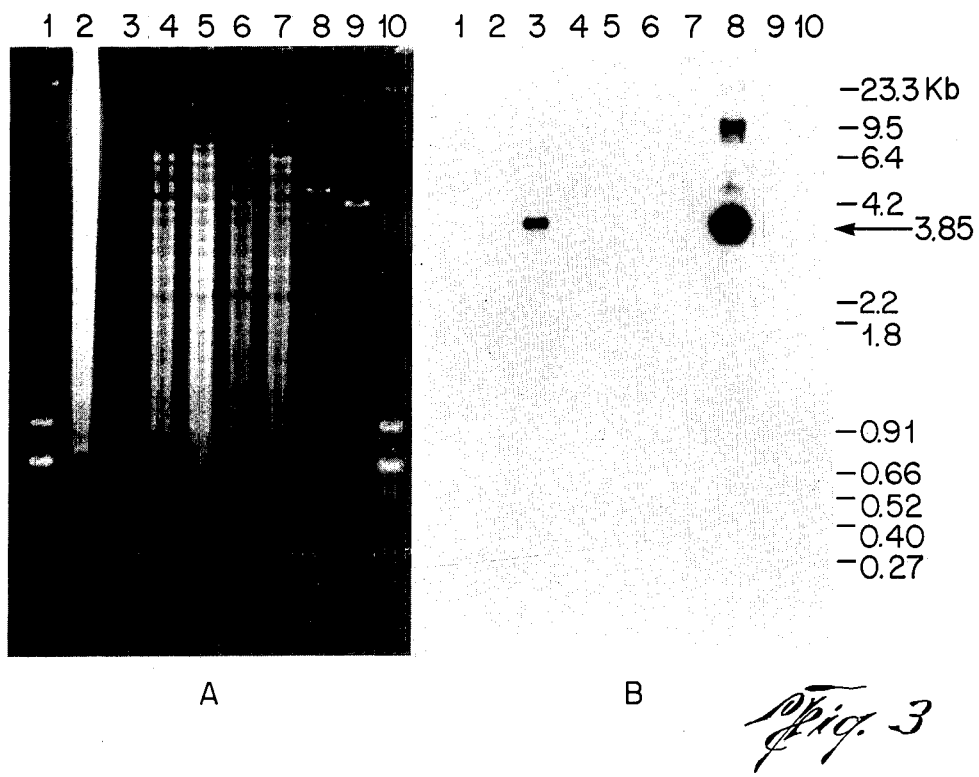
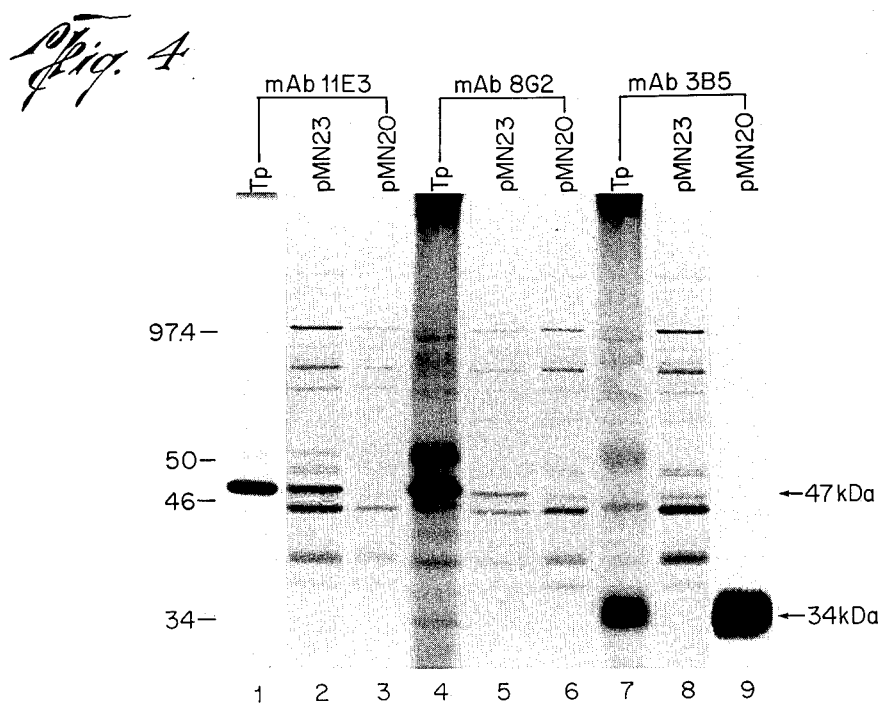

CLONING AND EXPRESSION OF THE 47-KILODALTON ANTIGEN OF TREPONEMA PALLIDUM

The United States government may have rights in the substance of this patent because of developmental work supported by the U.S. Department of Health and Human Services in the form of research grants 1-R01-AI-16692 and 1-R01-AI-17366 from NIH-NIAID.

BACKGROUND OF THE INVENTION

The present invention generally relates to the use of recombinant DNA technology to create a microorganism capable of producing antigens reactive with antibodies developed in response to Treponema pallidum. The production, by genetically engineered microorganisms, of the immunodominant 47–48 kilodalton surface antigen of Treponema pallidum,* generally referred to as the 47 kilodalton surface antigen, is a particular object of the present invention.

Infection by *Treponema pallidum* is the well-established cause of syphillis. Syphillis, despite the continued availability of effective antibiotics, continues to result in worldwide misery and morbidity. The inability to establish in vitro cultures of *Treponema pallidum* has restricted research studies of this organism. This microorganism is usually propagated by in vivo culture in hamster lymph nodes or rabbit testes, which are useful but not methods conducive to large-scale production of *Treponema pallidum* or the antigens thereof, particularly pure antigens. It has proven difficult to obtain *Treponema pallidum* antigens free of hamster or rabbit antigens from *Treponema pallidum* cultured in vivo. Thus, purified treponemal antigens have not been available from traditional techniques of microorganism production.

More modern techniques of molecular biology have been applied in relation to characterization and detection of *Treponema pallidum, Treponema pallidum* antigens and infection by *Treponema pallidum.* Various polyclonal and monoclonal antibodies to *Treponema pallidum* antigens have also been prepared.

U.S. Pat. No. 4,514,498, issued to Kettman and Norgard, Apr. 30, 1985 described numerous monoclonal antibodies directed toward antigens of *T. pallidum.* Two hybridoma clones 8G2 (ATCC HB8134) and 11E3 produced antibodies specific for the 47 kDa surface antigen of *T. pallidum.* These particular two antibodies were used in the present invention for the selection of *E. coli* clones producing the 47 kDa antigen.

Norgard et al. (1983) (*Infect. and Immun.,* V 42, pp 435–445) described construction of hybrid pBR322 plasmid clone banks in *E. coli* K-12 representing the entire—*Treponema pallidum* genome. Rabbit anti-*T. pallidum* serum was used in a radioimmuno-colony blot assay to detect *E. coli* clones synthesizing *T. pallidum* antigens. One clone was found to encode a gene product of 44 kDa. Either immune rabbit serum or human syphilitic serum was used to detect the *E. coli* clones producing the *T. pallidum* antigen. The methodological difference between this reference and the present disclosure begins to distinguish the present invention. Additionally, it has been found that monoclonal antibodies specific for the *T. pallidum* 47 kDa surface antigen were unable to react with the 44kDa antigen.

Stamm et al., (1982) (*Infect. and Immun.,* V 36, pp 1238–1241) described the establishment of a *T. pallidum* DNA clone bank. *T. pallidum* DNA was cleaved with Bam HI endonucleus and the cleavage fragments ligated to Bam HI-cleaved plasmid pBR322. Four transformed *E. coli* clones were noted as generally producing *T. pallidum* antigens.

Stamm et al. (1983) (*Infect. and Immun.,* V 41, pp 709–721) described the expression of *Treponema pallidum* Antigens in *Escherichia coli* K-12. Stamm et al. (1983) describe use of a pBR322 bank of recombinant plasmids harboring *Treponema pallidum* DNA inserts in *Escherichia coli* and identification of clones expressing *Treponema pallidum* antigens. The molecular weights of antigens produced by plasmid pLV32-transformed *E. coli.* were 25 kDa, 35 kDa and 39 kDa in size. An *E. coli* clone bearing plasmid pLV55 encoded a 35 kDa, *T. pallidum* protein antigen. An object of the Stamm et al. (1983) reference was to produce *T. pallidum* surface antigens. In the Stamm et al. (1983) reference whole human or rabbit serum against syphillis was used to select transformed *E. coli* clones.

Van de Donk et al. (1984) (in *Innovations in Biotechnology,* ed. by Houwink, et al., Elsevier Science, Amsterdam) described the development of hybridoma cell lines producing antibodies directed against *T. pallidum* antigens. It also discloses that certain monoclonal antibodies obtained from the hybridoma cell lines reacted with a 46 kDa and a 44 kDa polypeptide antigen of *Treponema pallidum.* Furthermore, the reference indicated that these monoclonal antibodies may be used for the purification of *Treponema pallidum* antigens produced by *E. coli* carrying *Treponema pallidum* recombinant DNA, as previously suggested by Norgard et al. (1983) (*Infect. and Immun.,* V 42, pp 435–445).

Van Embden et al., (1983) (*Infect and Immun.,* V 42, pp 187–196) described the production of *E. coli* K-12 clones transformed with plasmids bearing *T. pallidum* DNA. *E. coli* transformants were noted producing a variety of *T. pallidum* polypeptide antigens, including polypeptides with apparent sizes of 35 kDa, 41 kDa, 44 kDa, and 58 kDa, among others.

Coates et al. (1985) (Abstracts of the 85th Annual Meeting of the Amer. Soc. for Microbiol., Abstract C29, p 304) described an *E. coli* transformant producing an 18 kDa *T. pallidum* polypeptide antigen.

Fehniger et al., (1985) (Abstracts of the 85th Annual Meeting of Amer. Soc. for Microbiol., Abstract B156, p 44) described a 38 kDa hydrophobic *T. pallidum* antigen as produced by an *E. coli* transformed with a recombinant plasmid.

Rodgers et al., (1985) (Abstracts of the 85th Annual Meeting of Amer. Soc. for Microbiol., Abstract C30, p 305) described evaluation of the reactivity of a 37 kDa polypeptide *T. pallidum* antigen produced by an *E. coli* transformant.

PCT patent application (1984) number PCT/US83/01718 (International Publication Number WO84/01961 entitled "Recombinant DNA Derived Antigens of *Treponema Pallidum*" by Lovett) described *E. coli* transformant clones containing plasmid-bound *T. pallidum* DNA and expressing *T. pallidum* peptide antigens. Various clones produced antigens with molecular weights or weight ranges of: 16–20 kDa; 43 kDa; 37–46 kDa; 18–23 kDa; 150 kDa; or 180 kDa.

Potentially important antigens or immunogens of *T. pallidum* have been identified in several laboratories (Alderete et al. (1980) *Infect. Immun.,* V 30, pp 814–823; Baker-Zander et al. (1985) (*J. Infect. Dis.,* V 151, pp 264–272; Baker-Zander et al., (1983) *Infect. Immun.,* V 42, pp 634–638; Baker-Zander et al. (1984) *Infect. Immun.*, V 46, pp 116–121; Hanff et al., (1982) *J. Immunol.*, V 129, pp 1287–1291; Jones et al., (1984) *J. Exp. Med.*, V 160, pp 1404–1420; Lukehart et al., (1982) *J. Immunol.*, V 129, pp 833–838; Lukehart et al. (1986) *Sex. Trans. Dis.*, V 13, pp 9–15; Lukehart et al. (1985) *J. Immunol.*, V 134, pp 585–592; Marchitto et al. (1984) *Infect. Immun.*, V 45, pp 660–666,; Marchitto et al. (1986) *Infect. Immun.*, V 51, pp 168–176; Moskophidis et al. (1984) *Infect. Immun.*, V 43, pp 127–132; Norris et al. (1984) *J. Immunol.*, V 133, pp 2686–1692; Penn et al. (1985) *J. Gen. Microbiol.*, V 131, pp 2349–2357; Strugnell et al. (1986) *Infect. Immun.*, V 51, pp 957–960; Thornburg et al. (1983) *Infect. Immun.*, V 42, pp 623–627; Thornburg et al. (1985) *Genitourin. Med.*, V 61, pp 1–6; and van Eijk et al. (1982) *J. Microbiol.*, V 48, pp 486–497). Potential biological significance was previously assigned to a major, immunogenic surface antigen of *T. pallidum* having a molecular mass of 47 kilodaltons (kDa) (Jones et al., (1984) *J. Exp. Med.*, V 160, pp 1404–1420; and Marchitto et al. (1984) *Infect. Immun.*, V 45, pp 660–666). Biologically active monoclonal antibodies (mAbs), in combination with various in vitro and in vivo assays, were used to characterize the immunogen (Jones et al. (1984) *J. Exp. Med.*, V 160, pp 1404–1420; Marchitto et al. (1984) *Infect. Immun.*, V 45, pp 660–666; Marchitto et al. (1986) *Infect. Immun.*, V 51, pp 168–176; and Norgard et al. (1984) *J. Clin. Microbiol.*, V 20, pp 711–717). The 47 kDa antigen was shown to be: (i) surface-associated; (ii) abundant (Jones et al., (1984) *J. Exp. Med.*, V 160, pp 1404–1420; Marchitto et al. (1984) *Infect. Immun.*, V 45, pp 660–666; and Marchitto et al. (1986) *Infect. Immun.*, V 51, pp 168–176); (iii) highly immunogenic in both rabbits and humans (Baker-Zander et al. (1985) *J. Infect. Dis.*, V 151, pp 264–272; Hanff et al. (1982) *J. Immunol.*, V 129, pp 1287–1291; Jones et al. (1984) *J. Exp. Med.*, V 160, pp 1404–1420; Lukehart et al. (1986) *Sex. Trans. Dis.*, V 13, pp 9–15; Strugnell et al. (1986) *Infect. Immun.*, V 51, pp 957–960; and van Eijk et al. (1982) *J. Microbiol.*, V 48, pp 486–497); (iv) proteinaceous; (v) found in at least three subspecies of pathogenic *T. pallidum*, the etiological agents of veneral syphilis, endemic syphilis, and yaws; and (vi) absent in nonpathogenic, saprophytic treponemes (Jones et al., (1984) *J. Exp. Med.*, V 160, pp 1404–1420; Marchitto et al. (1984) *Infect. Immun.*, V 45, pp 660–666; Marchitto et al. (1986) *Infect. Immun.*, V 51, pp 168–176; and Norgard et al. (1984) *J. Clin. Microbiol.*, V 20, pp 711–717). Anti-47 kDa mAbs possess diagnostic value; they bind strongly in immunofluorescence assays to *T. pallidum* isolated from human syphilitic lesions. Anti-47 kDa mAbs also partially block the attachment of *T. pallidum* to host cells in vitro (Jones et al., (1984) *J. Exp. Med.*, V 160, pp 1404–1420). Anti-47 kDa mAbs bind to *T. pallidum* in the *T. pallidum* immobilization (TPI) assay, resulting in complement-dependent immobilization of motile organisms and these mAbs in the present of complement neutralize (kill) *T. pallidum* in the in vitro-in vivo neutralization test of Bishop and Miller (Bishop et al. (1986) *J. Immunol.*, V 117, pp 197–207; Jones et al., (1984) *J. Exp. Med.*, V 160, pp 1404–1420; and Marchitto et al. (1986) *Infect. Immun.*, V 51, pp 168–176).

The potential biological significance of the 47 kDa immunogen is supported by work on similar or identical immunogens. Lukehart et al. (Lukehart et al. (1982) *J. Immunol.*, V 129, pp 833–838) and Baker-Zander and Lukehart (Baker-Zander et al. (1983) *Infect. Immun.*, V 42, pp 634–638; and Baker-Zander et al. (1984) *Infect. Immun.*, V 46, pp 116–121) reported that a 48 kDa immunogen of *T. pallidum* contained *T. pallidum*-specific epitopes that could be detected in the treponemal pathogens *T. pallidum*, *T. pertenue* (yaws organism), *T. paraluis-cuniculi* (agent of rabbit veneral spirochaetosis) and *T. hyodysenteriae* (agent of swine dysentery). Lukehart also observed an early and significant humoral response to the 47 kDa immunogen of *T. pallidum* in patients infected with *T. carateum* (pinta organism) (S. A. Lukehart, personal communication). Hanff et al. (Hanff et al., (1982) J. Immunol., V 129, pp 1287–1291) showed an early humoral immune response during human syphilis to *T. pallidum* antigens having molecular masses from 45–47 kDa. Baker-Zander et al. (Baker-Zander et al. (1985) (*J. Infect. Dis.*, V 151, pp 264–272) confirmed the strong reactivity of syphilitic sera early in the course of human infection to a 48 kDa antigen of *T. pallidum*. This early and significant humoral immune response also was observed in experimental rabbits (Lukehart et al. (1986) *Sex. Trans. Dis.*, V 13, pp 9–15). van Eijk and van Embden (van Eijk et al. (1982) *J. Microbiol.*, V 48, pp 486–497) reported an early humoral immune response to a 46 kDa *T. pallidum* immunogen among humans with primary syphilis and later stages of the disease. Strugnell et al. (Strugnell et al. (1986) *Infect. Immun.*, V 51, pp 957–960) reported that the most vigorous humoral immune response detectable early in the experimental rabbit was directed against a polypeptide of 47 kDa. Thornburg and Baseman (Thornburg et al. (1983) *Infect. Immun.*, V 42, pp 623–627); and Thornburg et al. (Thornburg et al. (1985) *Genitourin. Med.*, V 61, pp 1–6) also described a major 45 kDa immunogen of *T. pallidum*, which was found in *T. pallidum* and *T. pertenue*. Penn et al. (Penn et al. (1985) *J. Gen. Microbiol.*, V 131, pp 2349–2357) recently concluded that *T. pallidum* contains an immunodominant, 47 kDa major outer membrane protein. Additionally, our earlier findings (Marchitto et al. (1986) *Infect. Immun.*, V 51, pp 168–176; and Norgard et al. (1984) *J. Clin. Microbiol.*, V 20, pp 711–717) that anti-47 kDa mAbs can be used diagnostically to detect relatively few *T. pallidum* has been confirmed by Lukehart et al. (Lukehart et al. (1985) *J. Immunol.*, V 134, pp 585–592) and Hook et al. (Hook et al. (1985) *J. Clin. Microbiol.*, V 22, pp 241–244). Hook et al. (Lukehart et al. (1986) *Sex. Trans. Dis.*, V 13, pp 9–15) also reported a correlation between early immune clearance of infecting *T. pallidum* and healing of the primary lesion in the experimental rabbit; it was postulated that primary lesion healing may be influenced by antibody directed against immunodominant molecules, such as the 47 kDa immunogen (Lukehart et al. (1986) *Sex. Trans. Dis.*, V 13, pp 9–15).

Using serum from *T. pallidum*-infected rabbits or murine mAbs directed against the 47 kDa immunogen of *T. pallidum*, it was previously reported that the 47 kDa immunogen was pathogen-specific (Jones et al., (1984) *J. Exp. Med.*, V 160, pp 1404–1420; Marchitto et al. (1984) *Infect. Immun.*, V 45, pp 660–666; Marchitto et al. (1986) *Infect. Immun.*, V 51, pp 168–176; and Norgard et al. (1984) *J. Clin. Microbiol.*, V 20, pp 711–717); the presence of an analogous 47 kDa antigen was not detected in the nonpathogenic trephonemes *T. phagedenis* biotype Reiter, *T. denticola*, *T. scoliodontum*, *T. vincentii*, or *T. refringens* using immune rabbit serum or mAbs directed against the 47 kDa immunogen. Lukehart et al. (Lukehart et al., (1982) *J. Immunol.*, V 129, pp 833-383; Lukehart et al. (1985) *J. Immunol.*, V 134, pp 585-592) postulated that a 48 kDa *T. pallidum* immunogen may possess "pathogen-specific" determinants may be located on separate polypeptides which co-migrate in polyacrylamide gels. When either a 3.85 kb HindIII DNA fragment of the 5.4 kb encoding sequence or intact hybrid plasmid DNA (containing the entire 5.4 kb encoding sequence) were used as DNA hybridization probes under moderate or low DNA hybridization stringency, no hybridization with any homologous DNA fragment of the nonpathogenic treponemes was observed. Further, mAb C2-1 of Lukehart, directed against a "common" treponemal epitope of a 47 kDa immunogen (Hook et al. (1985) *J. Clin. Microbiol.*, V 22, pp 241-244; and Lukehart et al. (1985) *J. Immunol.*, V 134, pp 585-592), failed to react with the 47 kDa immunogen-expressing clones of the present invention, while the pathogen-specific mAb H9-1 (Hook et al. (1985) *J. Clin. Microbiol.*, V 22, pp 241-244, Lukehart et al. (1985) *J. Immunol.*, V 134, pp 585-592) reacted with these clones. Thus, genetic and immunologic data provided here support the existence of a pathogen-specific 47 kDa immunogen.

The cloning and expression of the *T. pallidum* 47 kDa immunogen gene in *Escherichia coli* is described herein as a component of the present invention.

The contents of the above-described references are incorporated by reference herein for their descriptions of microorganisms, materials and methods established in the field.

SUMMARY OF THE INVENTION

Monoclonal antibodies directed against the 47 kDa major outer membrane surface immunogen of virulent *Treponema pallidum* were used to select *E. coli* recombinant clones expressing the 47 kDa immunogen. The phenotype of the clones was dependent on the presence of recombinant plasmid in the host cell. Southern hybridization revealed that the cloned *T. pallidum* DNA sequence was an accurate representation of the *T. pallidum* genomic DNA arrangement. Purified IgG from rabbits experimentally infected with *T. pallidum* or human secondary syphilitic sera specifically reacted with the clones while normal human serum or IgG from normal rabbit serum did not. Results of Southern hybridization indicated that a homologous 47 kDa immunogen gene was absent in at least 4 species of nonpathogenic treponemes tested, as well as from total rabbit genomic DNA. Rabbit anti-*T. phagedenis* biotype Reiter (treponemal nonpathogen) antiserum and a monoclonal antibody directed against a "common" treponemal determinant were unreactive with the clones. Western blotting and radioimmunoprecipitation experiments with specific monoclonal antibodies revealed that the recombinant (*E. coli*) and native (*T. pallidum*) forms of the antigen had identical electrophoretic mobilities. The availability of recombinant 47 kDa immunogen provides a new opportunity for biochemical analysis of the protein, structure-function studies, examination of its role in microbial pathogenesis, and direct assessment of its diagnostic and vaccinogenic potentials.

BRIEF DESCRIPTION OF THE DRAWINGS

FIG. 3. Southern blot hybridization of HindIII-restricted genomic DNAs and recombinant plasmid pMN23 encoding the 47 kDa immunogen of *T. pallidum*. Panel A: 1% agarose gel containing HindIII-restricted genomic DNA of rabbit (lane 2), *T. pallidum* (lane 3), *T. denticola* (lane 4), *T. phagedenis* (lane 5), *T. scoliodontum* (lane 6), *T. vincentii* (lane 7), recombinant plasmid pMN23 (lane 8), and plasmid pBR322. Lanes 1 and 10 contain combined pBR322-AluI and bacteriophage lambda-HindIII molecular weight markers. B: Southern Blot of Panel A; a fragment of plasmid DNA from clone pMN23 was used as the labeled hybridization probe. Note the presence of the 3.85 kb homologous DNA HindIII-fragment present only in *T. pallidum* genomic DNA (lane 3) and the recombinant plasmid pMN23 (lane 8).

FIG. 4. Radioimmunoprecipitation of the 47 kDa immunogen of *T. pallidum* from $^{125}$I-labeled *T. pallidum* and $^{35}$S-labeled *E. coli* recombinant clone pMN23. Lanes 1-3, 4-6, and 7-9 were immunoprecipitated with mAbs 11E3, 8G2, and 3B5 (control), respectively. Lanes 1, 4, and 7 contained $^{125}$I-labeled *T. pallidum* antigens. Lanes 2, 5, and 8 contained $^{35}$S-labeled products from the 47 kDa immunogen-expressing clone pMN23. Lanes 3, 6, and 9 contained $^{35}$S-labeled products from clone pMN20, which expresses a 34 kDa immunogen of *T. pallidum* recognized by mAb 3B5. Protein molecular weights are indicated on the left (in kDa), derived from $^{14}$C-molecular weight markers electrophoresed on the gel. Arrows indicate the location of the 47 kDa and 34 kDa immunogens.

DESCRIPTION OF THE PREFERRED EMBODIMENTS

Figure 1:
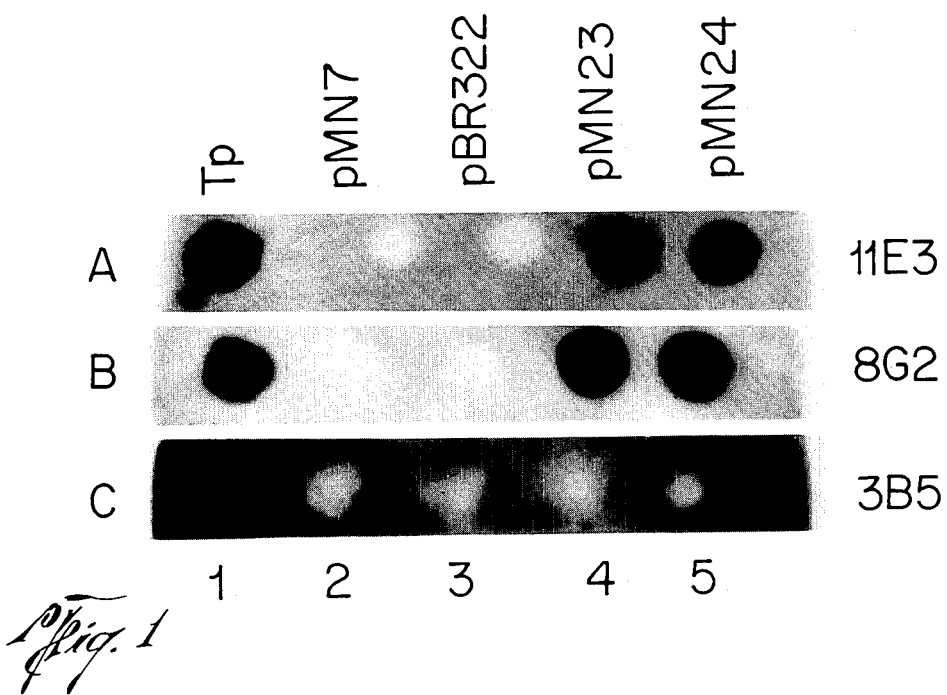
FIG. 1. Radioimmuno-colony blot assay of *E. coli* recombinant DNA clone colonies expressing the 47 kDa surface immunogen of *T. pallidum*. *T. pallidum* cells (lane 1) were spotted onto each filter as a positive control. Negative control clones included pMN7 (lane 2) and pBR322 in *E. coli* RR1 (lane 3). Filteres were reacted with mAbs 11E3 (row A), 8G2 (row B), and 3B5 (row C) (negative control), prior to probing with $^{125}$I-labeled rabbit anti-mouse IgG.

The present invention involves the use of a clone bank produced by conventional recombinant DNA techniques involving insertion of *Treponema pallidum* DNA fragments into a suitable vector and transferring the DNA fragments into a microorganism recipient. Although any clone bank comprising *Treponema pallidum* DNA may be utilized, the preestablished (June 9, 1982) pBR322 hyrbid clone bank described by the inventor was used as a preferred source of recombinant *E. coli* clones (Norgard et al. (1983), *Infection and Immu-* nity, 42 435-445). This clone bank of microorganisms were screened for clones producing a particular *Treponema pallidum* antigen. The screening was performed by observing interactions of clone colonies with antibodies specifically binding to the *Treponema pallidum* antigen of interest. Clones producing antigen of interest were selected, separated and propagated to produce *Treponema pallidum* antigen for further identification, characterization or use. This use may be, for example, in the detection of antibodies to *Treponema pallidum* or in the production of a vaccine useful for the induction of immunity to syphilis.

The present invention comprised a process for preparing microbial clones expressing the 47 kDa surface immunogen of *Treponema pallidum*. Initially the DNA of a microbial vector is cleaved, preferably by a restriction endonuclease, to produce a first DNA fragment. Said first DNA fragment is combined with a second DNA fragment, the second DNA fragment being from *Treponema pallidum*. Said first and second DNA fragments are characterized as being capable of recombination, and a recombinant vector bearing *Treponema pallidum* DNA is ligatively formed. In the next step, a suitable microbial host is transfected with said recombinant vector to produce microbial clones expressing *Treponema pallidum* antigens. These microbial clones are then cultivated, preferably on the surface of a nutrient agar, to form visible colonies. The colonies are then contacted with an antibody having a specific affinity for the 47 kDa surface immunogen of *Treponema pallidum*. Microbial clone colonies having an affinity for the antibody are then identified and selected. Said selected colonies are characterized by their expression of the 47 kDa surface immunogen of *Treponema pallidum*.

The 47 kDa surface immunogen described above may be defined by having a specific affinity for monoclonal antibody produced by murine hybridoma cell line 8G2 (American Type Culture Collection deposit number HB8134). Although most workers in the field have agreed on the 47 kDa size of this *Treponema pallidum* immunodominant surface immunogen, such weight determinations may vary to a minor extent. The microbial vector is most preferably a plasmid although other usable vectors such as many phages are well known in the art. The most preferred microbial vector is plasmid pBR322. In the above-described process, the microbial vector is preferably cleaved with PstI and dG-tailed to form the first DNA fragment. In practice, the above-described process involves use of a monoclonal antibody as an antibody for identification and selection of clone colonies producing the 47 kDa surface immunogen. A most preferred monoclonal antibody is that produced by murine hybridoma cell line 8G2 (American Type Culture Collection number HB8134).

A microbial host particularly preferred in the practice of this invention is of the species *Escherichia coli*. The second DNA fragment used for the formation of a recombinant vector for the creation of recombinant microorganisms is preferably from a partial restriction enzyme digest of *Treponema pallidum* or other pathogenic subspecies of Treponema. The second DNA fragment is preferably obtained from this partial restriction enzyme digest and tailed with dC residues.

The recombinant plasmid adapted for transformation of a microbial host and formation of a *Treponema pallidum* immunogen most preferably comprises a plasmid vector into which a deoxyribonucleic acid (DNA) segment which codes for the 47 kDa surface immunogen of *Treponema pallidum* has been inserted. The transformant microorganisms of the present invention are those which include a recombinant plasmid comprising a plasmid vector into which a DNA segment which codes for the 47 kDa surface immunogen of *Treponema pallidum* has been inserted. The inserted *Treponema pallidum* DNA segment coding for the 47 kDa surface immunogen is shown as a 5.4 kb partially restriction enzyme-mapped fragment in FIG. 2.

The presence of antibodies to *Treponema pallidum* in biological fluids may be detected by processes of the present invention. A sample of biological fluid is first obtained and then a 47 kDa surface immunogen of *Treponema pallidum* produced by the recombinant DNA techniques of the present invention are added to the sample of biological fluid. Then, whether said immunogen reacts with antibodies to *Treponema pallidum* present in said sample may be determined by any of the numerous immunological methods for such determinations well known in the field.

A process for immunizing individuals against infection by *Treponema pallidum* is also comprised by the present invention. The immunization process comprises obtaining an amount of the 47 kDa surface immunogen of *Treponema pallidum* from a recombinant microorganism producing said immunogen. The next step is to administer said immunogen to an individual in an amount and manner eliciting formation of antibodies or induction of cell-mediated immunity by the individual to the 47 kDa surface immunogen of *Treponema pallidum*.

A microorganism of the strain of *Escherichia coli* capable of producing the 47 kDa surface immunogen of *Treponema pallidum* has been produced by the processes of the present invention and has been deposited with the American Type Culture Collection, Rockville, MD as ATCC Deposit No. 67204. This microorganism has an identifying characteristic of being reactive with antibodies to *Treponema pallidum*, particularly antibody to the 47 kDa surface immunogen of *Treponema pallidum*. A 47 kDa antigen reactive with antibodies to *Treponema pallidum* and produced by a recombinant microorganism such as the strain of *Escherichia coli* having the ATCC Deposit No. 67204 is also specifically comprised by the present invention.

Such 47 kDa recombinant-synthesized antigens, identified by molecular mass (size) and immunological characteristics (binding of monoclonal antibodies 8G2 [ATCC No. HB-8134] and 11E3 [U.S. Pat. No. 4,514,498 and U.S. patent application Ser. No. 702,327]) as the B 47 kDa surface immunogen of *Treponema pallidum*, may be used to prepare unique compositions of matter useful in the diagnosis of or vaccination against pathogenic treponemal infections such as by *Treponema pallidum* or other pathogenic subspecies of Treponema.

A process for detecting the presence of *Treponema pallidum* in a clinical sample may be devised using the nucleotide fragments of the present invention including those coding for the 47 kDa surface immunogen of *Treponema pallidum*. Such nucleotide fragments are included within the 5.4 kb insert of plasmid pMN23 shown in FIG. 2. This plasmid has been deposited with the American Type Culture Collection 12301 Park Lawn Drive, Rockville, Md., 20852, on Sept. 30, 1986 as ATCC Deposit No. 67204. Labeled nucleotide fragments may be prepared directly from the 5.4 kb insert or from complementary nucleotide fragments synthesized from the nucleotide sequences of that insert. A 1.28 kb fragment between about the ClaI cleavage site and the second internal PstI cleavage site appeared to represent the smallest fragment (discounting any leader sequences) actually coding the 47 kDa structural surface immunogen. In practice the methods and reagents described in U.S. Pat. No. 4,358,535, which is incorporated by reference herein, may be utilized but with the above-described *Treponema pallidum* nucleotide fragments or nucleotide sequences contained therein.

Initially clinical samples from a patient are deposited on an inert support. Said deposited sample is then treated to affix genetic material of any pathogenic *Treponema pallidum* present in said sample to the support in substantially single stranded form at substantially the same site on the support where said sample was deposited. The fixed single stranded genetic material is then contacted with a labeled probe having at least about 25 bases substantially complementary to a nucleotide sequence of *Treponema pallidum* coding for the 47 kDa surface immunogen. This contacting is under hybridizing conditions at a predetermined stringency. Duplex formation on said support between affixed *Treponema pallidum* DNA and the labeled probe may be detected by measuring the amount of the label bound to the solid support.

The *Treponema pallidum* antigen of particular interest in this invention was the 47 kiloDalton (kDa) surface immunogen previously described (Jones et al. (1984) *J. Exp. Med.*, V 160, pp 1404–1420) and Marchitto et al. (1984) *Infect. Immun.*, v 45, pp 660–666). To screen for recombinant clones producing the 47 kDa antigen, monoclonal antibodies specifically binding this antigen were used. These antibodies and the hybridomas producing them (8G2 ATCC deposited with the American Type Culture Collection, 12301 Park Lawn Drive, Rockville, Md., 20852 on May 20, 1982 as HB 8134 and 11E3) are described in U.S. Pat. No. 4,514,498 and pending U.S. patent application Ser. No. 702,327.

MATERIALS AND METHODS

Bacterial Strains, Plasmids, and DNAs. The virulent Nichols strain of *Treponema pallidum* subspecies *pallidum* (*T. pallidum*) was used as the representative pathogen in this study. It was maintained and cultivated in the testicles of New Zealand white rabbits as previously described (Norgard et al. (1983) *Infect. Immun.*, V 42, pp 435–445 and Robertson et al. (1982) *Infect. Immun.*, V 36, pp 1076–1085). Nonpathogenic strains of treponemes *T. phagedenis* biotype Reiter, *T. denticola, T. scoliodontum,* and *T. vincentii* were cultived in vitro (Swancutt et al. (1986) *Infect. Immun.*, V 52, pp 110–119). *Escherichia coli* RR1 was used as the recipient host strain for cloning the transformation experiments (Swancutt et al. (1986) *Infect. Immun.*, V 52, pp 110–119). A summary of the relevant recombinant plasmids used in this study is given in Table 1.

TABLE 1

| Plasmid/ Strain | Characteristics of Recombinant Plasmids<br>T. pallidum DNA insert (kb) | Immunogen expressed (kDa) | Relevant mAb or polyclonal antibody reactivity | Reference |
|---|---|---|---|---|
| pBR322 | none | none | none | c |
| pMN7/RICB2-1 | 3.7 | 44[a] | IRS[b] | c |
| pMN20 | 1.75 | 34 | 3B5, 9B12, 10G2 | d |
| pMN23 | 5.4 | 47 | 11E3, 8G2 | this report |
| pMN24 | 5.4 | 47 | 11E3, 8G2 | this report |

[a]Unrelated to the 47 kDa antigen of clones pMN23 and pMN24, as shown by mAb and genetic studies.
[b]Immune rabbit serum obtained from T. pallidum-infected rabbits.
[c](Norgard et al. (1983) Infect. Immun., V 42, pp 435–44)
[d](Swancutt et al. (1986) Infect. Immun., V 52, pp 110–119)

*E. coli* RR1 harboring the plasmid pMN7 (old designation: RICB2-1) has been described (Norgard et al. (1983) *Infect. Immun.*, V 42, pp 435–445); pMN7 originated from the clone bank referenced below and it contains a 3.7-kilobase (kb) DNA insert of *T. pallidum* DNA cloned by GC-tailing into the PstI site of pBR322. It encodes a 44 kDa recombination antigen unrelated to the 47 kDa antigen. The 44 kDa antigen of the clone pMN7 is immunoprecipitable by immune rabbit serum (Norgard et al. (1983) *Infect. Immun.*, V 42, pp 435–445) but not by any of our current mAbs. Clone pMN20, encoding and expressing a 34 kDa surface antigen of *T. pallidum,* has been described (Swancutt et al. (1986) *Infect. Immun.*, V 52, pp 110–119). All plasmid derivatives were propagated in *E. coli* RR1 and isolated and purified according to Norgard (Norgard (1981) *Anal. Biochem.*, V 113, pp 34–42). New Zealand White normal male rabbit liver DNA and treponemal DNAs were isolated as previously described (Norgard et al. (1981) *Science,* V 213, pp 553–555).

Cloning Procedures and Restriction Enzyme Analyses. A pre-established pBR322 hybrid plasmid clone bank (June 9, 1982) was used as the potential source of antigen-expressing clones (Norgard et al. (1983) *Infect. Immun.*, V 42, pp 435–445). The bank was constructed using combined AluI and HaeIII partial restriction enzyme digests of *T. pallidum DNA which was subsequently tailed with dC residues and cloned into pBR*322 (dG-tailed at the PstI site to regenerate PstI sites flanking the cloned inserts) (Norgard et al. (1983) *Infect. Immun.*, V 42, pp 435–445). Restriction enzymes for the analysis of plasmids and digestion of genomic DNA were purchased from New England Biolabs (Beverly, MA).

Radiolabeling of Bacteria, DNA, and Proteins. *T. pallidum* was purified from rabbit testicular tissue by the Percoll density gradient method (Hanff et al. (1984) *Sex. Trans. Dis.*, V 11, pp 275–286); bacteria were radiolabeled with Na-$^{125}$I using a lactoperoxidase method (Alderete et al. (1980) (*Infect. Immun.*, V 30, pp 814–823, Jones et al., (1984) *J. Exp. Med.*, V 160, pp 1404–1420). Strains of *E. coli* RR1 harboring various pBR322 plasmid derivatives were metabolically labeled with L-$^{35}$S-methionine as previously described (Norgard et al. (1983) *Infect. Immun.*, V 42, pp 435–445). All probe DNA was radiolabeled with alpha-$^{32}$P-dCTP using the nick translation kit of New England Nuclear (Boston, MA). Antibody probes were radiolabeled with Na-$^{125}$I using a chloramine T method (Hunter et al. (1962) *Nature*, V 194, pp 495–496).

Southern Gel Hydbridizations. Southern blots were performed according to the previously published method (Norgard et al. (1981) *Science*, V 216, pp 553–555, Southern (1975) *J. Mol. Biol.*, V 98, pp 503–517, (Swancutt et al. (1986) *Infect. Immun.*, V 52, pp 110–119). For one probe, a DNA restriction enzyme fragment was isolated from low melt agarose by Elutip TM (Schleicher & Schuell, Keene, NH) affinity chromatography (Schmitt et al. (1983) *Anal. Biochem.*, V 13, pp 462–464). Hybridization with DNA probes was carried out in 2X Denhardt's solution (Southern (1975) *J. Mol. Biol.*, V 98, pp 503–517) plus 6X SSC buffer (1X SSC=0.15M NaCl+0.015M sodium citrate, pH 7.0), 1 mM EDTA, and 100 ug/ml of sheared, denatured, salmon sperm DNA (Southern (1975) *J. Mol. Biol.*, V 98, pp 503–517). After hybridization for 16 hr at 68° C., filters were washed 3 times (30 min per wash) at room temperature with 500 ml portions of 2X SSC+0.1% sodium dodecyl sulfate followed by an additional 3 washes at room temperature (30 min per wash) using 500 ml portions of 0.1X SSC+0.1% sodium dodecyl sulfate. Filters were dried and subjected to autoradiography (Laskey (1977) *FEBS Lett.*, V 82, pp 314–316).

Monoclonal Antibodies, Antisera, and Antibody Probes. Murine mAbs 8G2 (IgG1), 11E3 (IgG2a), and 3B5 (IgG1) directed specifically against *T. pallidum* were generated, maintained, and characterized as previously described (Jones et al. (1984) *J. Exp. Med.*, V 160, pp 1404–1420; Marchitto et al. (1984) *Infect. Immun.*, V 45, pp 660–666; Marchitto et al. (1986) *Infect. Immun.*, V 51, pp 168–176; Norgard et al. (1984) *J. Clin. Microbiol.*, V 20, pp 711–717; Robertson et al. (1982) *Infect. Immun.*, V 36, pp 1076–1085; and Swancutt et al. (1986) *Infect. Immun.*, V 52, pp 110–119). Mab 11E3 has been described in detail (Jones et al. (1984) *J. Exp. Med.*, V 160, pp 1404–1420; Marchitto et al. (1984) *Infect. Immun.*, V 45, pp 660–666; Marchitto et al. (1986) *Infect. Immun.*, V 51, pp 168–176; and Norgard et al. (1984) *J. Clin. Microbiol.*, V 20, pp 711–717). MAbs 8G2 and 11E3 are directed against the major 47 kDa immunogen (Jones et al., (1984) *J. Exp. Med.*, V 160, pp 1404–1420, Marchitto et al. (1984) *Infect. Immun.*, V 45, pp 660–666). MAb 3B5 reacts with a 34 kDa surface immunogen of *T. pallidum* (Swancutt et al. (1986) *Infect. Immun.*, V 52, pp 110–119).

MAbs were used within in vitro hybridoma clone supernatants or were affinity purified from hybridoma clone supernatants using individual protein A-Sepharose columns (Ey et al. (1978) *Immunochemistry*, V 15, pp 429–436). MAbs C2-1 (IgM) and H9-1 (IgG1), were directed against "common" and "pathogen-specific" epitopes of *T. pallidum*, respectively (Hook et al. (1985) *J. Clin. Microbiol.*, V 22, pp 241–244, Lukehart et al. (1985) *J. Immunol.*, V 134, pp 585–592). Normal rabbit serum was collected from Venereal Disease Research Laboratory-nonreactive New Zealand white male rabbits. Rabbit anti-*T. pallidum* serum (immune rabbit serum) was obtained and pooled from 4 animals 3 to 12 months following a firm orchitis in both testicles after *T. pallidum* intratesticular infection; immune rabbits were shown to be "chancre immune" when challenged intradermally with $1 \times 10^5$ motile *T. pallidum* per site (Jones et al., (1984) *J. Exp. Med.*, V 160, pp 1404–1420). Rabbit anti-*T. phagedenis* biotype Reiter antiserum was provided by S. A. Lukehart. Seven human secondary syphilitic serum samples were provided by Dr. George Wendel; these sera were collected for routine serological diagnostic confirmation (within the past year) from females with confirmed secondary syphilis. Excess serum from each patient, stored at −70° C. and used in this study, was obtained from the clinical laboratory in lieu of regular discard by the laboratory. IgG was isolated from sera using sodium sulfate precipitation and DEAE cellulose column chromatography.

Radioimmuno-Colony Blot Assay. The radioimmunocolony blot (RICB) assay for the detection of *E. coli* clone colonies synthesizing *T. pallidum* antigens was carried out according to Norgard and Miller (Norgard et al. (1983) *Infect. Immun.*, V 42, pp 435–445) with minor modifications (Swancutt et al. (1986) *Infect. Immun.*, V 52, pp 110–119).

Radioimmunoprecipitation. Radioimmunoprecipitation (RIP) was performed as previously described (Swancutt et al. (1986) *Infect. Immun.*, V 52, pp 110–119) with minor modifications. For the radioimmuno-precipitation of *T. pallidum*, approximately $5 \times 10^6$ counts per min of $^{125}$I-labeled treponemes (1–3 counts per min per treponeme) were incubated in 1.0 ml of solubilization buffer (10 mM Tris-HCl [pH 7.8], 150 mM NaCl, 10 mM EDTA, and 0.2% Zwittergent 3-12 [Calbiochem-Behrine Corp., La Jolla, CA]. For $^{35}$S-methionine labeled *E. coli*, about $7 \times 10^7$ counts per min were used. Ten ug of goat anti-mouse IgG was added after the primary mAb (30 min at 4° C. with agitation) as a bridge for IgG1 mAbs 8G2 and 3B5. Solubilized immunoprecipitates were ultimately subjected to sodium dodecyl sulphate-polyacrylamide el (10%) electrophoresis after reducing at 100° C. in 5% 2-mercaptoethanol (Swancutt et al. (1986) *Infect. Immun.*, V 52, pp 110–119). $^{14}$C-labeled molecular weight markers were used as previously described (Swancutt et al. (1986) *Infect. Immun.*, V 52, pp 110–119). Different radiolabled compounds ($^{35}$S, $^{14}$C, and $^{125}$I) were detected on the same gel after treatment with EnHance (New England Nuclear Corp.) for $^{35}$S and $^{14}$C, followed by autoradiography (Laskey (1977) *FEBS Lett.*, V 82, pp 314–316).

Western Blots. Western blots were performed as previously described (Marchitto et al. (1984) *Infect. Immun.*, V 45, pp 660–666). For the analysis of *T. pallidum* antigens, approximately $1 \times 10^7$ solubilized treponemes per polyacrylamide gel lane were blotted. For *E. coli* recombinant derivatives, approximately $1 \times 10^8$ solubilized *E. coli* per gel lane were used.

RESULTS

Identification of Antigen-Expressing Clones. FIG. 1 shows the results of RICB assays using mAbs. Two recombinant DNA clones, pMN23 and pMN24, were isolated which reacted with anti-47 kDa mAbs 11E3 and 8G2, but not with the negative control mAb 3B5. All 3 mAbs failed to react with the negative control clones pMN7 and pBR322. Mab 3B5, directed against a 34 kDa surface immunogen of *T. pallidum* (Swancutt et al. (1986) *Infect. Immun.*, V 52, pp 110–119), reacted only with *T. pallidum*.

Immune rabbit serum IgG reacted in the RICB assay with clones pMN23, pMN24, and pMN7, as expected, while IgG from normal rabbit serum did not (not shown). Rabbit anti-*T. phagedenis* biotype Reiter antiserum, possessing antibodies against common treponemal determinants, also failed to react with clones pMN23 and pMN24 (not shown). MAb H9-1, directed specifically against the 47 kDa immunogen (Hook et al. (1985) *J. Clin. Microbiol.*, V 22, pp 241-244, Lukehart et al. (1985) *J. Immunol.*, V 134, pp 585-592), reacted strongly with clones pMN23 and pMN24, but not with pMN7 or PBR322 (not shown). In additional RICB assays, mAb C2-1, directed against a common treponemal epitope (Hook et al. (1985) *J. Clin. Microbiol.*, V 22, pp 241-244, Lukehart et al. (1985), *J. Immunol.*, V 134, pp 585-592), reacted with *T. pallidum* and *T. phagendenis* biotype Reiter, but not with any *E. coli* clones (not shown).

Further support for the plasmid-encoded, antigen-expressing phenotype was demonstrated by the fact that purified plasmid DNA from RIBC-positive recombinant clones was capable of transforming the 47 kDa antigen-expressing phenotype to normal *E. coli* host cells at a frequency of 100% (200 ot 200 random transformants tested).

Figure 2:
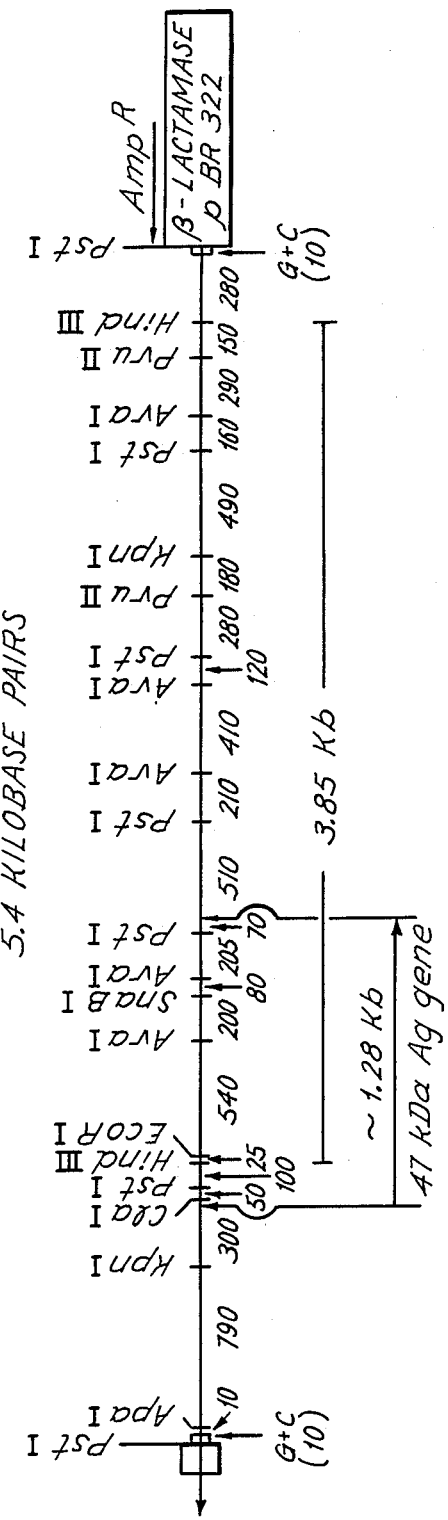
FIG. 2. Partial restriction enzyme map of the 5.4 kb insert of pMN23 encoding the 47 kDa immunogen of *T. pallidum*. The EcoRI site of pBR322 is located to the right of the figure. The direction of transcription for the 47 kDa antigen gene appears to be from left to right, opposite that of the beta-lactamase gene. The insert is flanked by PstI sites just outside short GC tails, and possesses a 3.85 kb internal HindIII fragment.

Restriction Enzyme Map of the 47 kDa Immunogen-Expressing Clone pMN23. FIG. 2 shows a preliminary restriction enzyme map of the 5.4 kb insert of plasmid pMN23. The pMN23 insert is flanked by short dGC tails inside PstI sites, with 5 internal PstI sites located within the insert. A strategic fragment for structural analysis of the 47 kDa immunogen encoding region included a 3.85 kb HindIII fragment; subcloning of this fragment into the HindIII site of pBR322, however, failed to result in expression of the relevant epitope(s) when 54 ampicillin-resistant, tetracycline-sensitive, 3.85 kb HindIII fragment-containing subclones were tested in the RICB assay using mAbs 11E3 or 8G2. Analogous restriction enzyme mapping of clone pMN24 revealed the presence of restriction enzyme fragments similar to those of pMN23. Thus, pMN23 and pMN24 may be identical.

Specificity of the Cloned 47 kDa Immunogen Gene Sequence Among *T. pallidum* DNA. Due to the potential presence of contaminating rabbit host DNA in *T. pallidum* DNA preparations used as a source of DNA for cloning, it was essential to establish the *T. pallidum* origin of the cloned DNA sequence. It also was important to determine if homologous gene sequences existed among immunologically-related, nonpathogenic treponemes. To address these possibilities, the 3.85 kb HindIII fragment of pMN23 was isolated, labeled, and used as a hybridization probe in Southern blot analysis (FIG. 3B). The agarose gel (1%) (FIG. 3A) contained HindIII-restricted preparations of genomic DNAs from *T. pallidum*, rabbit liver, and four nonpathogenic treponemes. Gel lanes 2 and 4-7 of FIG. 3A, containing other than *T. pallidum* DNA, were overloaded to ensure a conclusive result. In lanes 3 and 8 of FIG. 3B, the 3.85 kb HindIII probe hybridized to a 3.85 kb HindIII fragment of *T. pallidum* DNA and to itself; no hybridization with rabbit DNA, the DNAs of four nonpathogenic treponemes, or control DNA (lambda or pBR322) was observed. Multiple hybridizing bands observed in HindIII-cleaved pMN23 (FIG. 3B, lane 8) represented the minute proportion of pMN23 not completely restricted by HindIII treatment.

When Southern blots identical to FIG. 3B were probed and washed less extensively to the point where nonhomologous DNA-DNA hybridization could be observed to occur with either lambda DNA or pBR322 DNA, no hybridization of the 3.85 kb HindIII fragment probe with any HindIII DNA fragment of the nonpathogenic treponemes was observed (not shown). Intact plasmid pMN23 (containing the entire 5.4 kb sequence) used as a labeled probe under reduced stringency also did not hybridize to any HindIII DNA fragment of the nonpathogens (not shown). The inability to detect a homologous 47 kDa immunogen gene sequence in the nonpathogenic treponemes, therefore, did not appear to be the result of overly stringent hybridization conditions used in the Southern blot.

When Southern gel blots identical to FIG. 3B were probed with labeled pBR322 (vector DNA), no hybridization of a 3.85 kb HindIII fragment with *T. pallidum* DNA or with the 3.85 kd HindIII fragment of clone pMN23 was observed (not shown). In contrast, intact labeled pMN23 plasmid DNA used as a hybridization probe hybridized to the corresponding *T. pallidum* DNA sequence in both *T. pallidum* genomic DNA and clone pMN23, as well as to the pBR322 DNA sequences, but not to rabbit DNA or the genomic DNAs of the nonpathogenic treponemes, as predicted (not shown).

Expression of the 47 kDa Immunogen in *T. pallidum* and *E. coli*. FIG. 4 shows the results of RIP assays performed using $^{125}$I-labeled *T. pallidum* and $^{35}$S-labeled recombinant clones pMN23 and pMN20 as antigens. Solubilized antigens were immunoprecipitated using mAbs 11E3, 8G2, and 3B5. MAb 3B5, directed against a 34 kDa immunogen of *T. pallidum* (lane 7), was used as a control. MAbs 11E3 and 8G2 immunoprecipitated the 47 kDa immunogen from $^{125}$I-labeled *T. pallidum* (FIG. 4, lanes 1, 4). An antigen with an apparently identical $M_r$ to the 47 kDa immunogen of *T. pallidum* was immunoprecipitated by mAbs 11E3 and 8G2 from clone pMN23 (lanes 2, 5), but not from *E. coli* harboring the control hybrid plasmid pMN20 (Lanes 3, 6), which encodes a 34 kDa *T. pallidum* antigen (lane 9). In lanes 1, 4, and 7, the extraneous band at the molecular mass of 50 kDa represents rabbit host heavy chain immunoglobulin which copurifies with *T. pallidum* and which is labeled by lactoperoxidase-catalyzed iodination (Marchitto et al. (1986) *Infect. Immun.*, V 51, pp 168-176); other irrelevant bands in lanes 1-9 are due to nonspecific absorption of labeled products to *S. aureus* cells.

Figure 5:
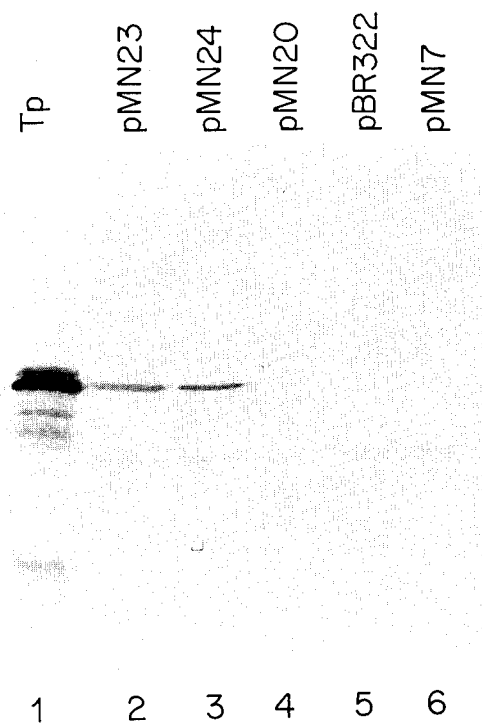
FIG. 5. Western blot of the 47 kDa immunogen expressed by recombinant clones pMN23 and pMN24. Solubilized antigens were detected after gel electrophoresis and protein transfer by incubation wth anti-47 kDa mAb8G2, which produced its characteristic reactivity profile with the 47 kDa *T. pallidum* immunogen (lane 1). Lanes 2 and 3 contained the 47 kDa immunogen-expressing clones pMN23 and pMN24, respectively. Lanes 4, 5, and 6 contained the 34 kDa immunogen-expressing clone pMN20, pBR322 in *E. coli* RR1, and the 44 kDa immqngen-expressing clone pMN7, respectively, as negative controls.

An analogous result to that of the RIP was obtained using Western blotting (FIG. 5). Anti-47 kDa mAb 8G2 reacted with 47 kDa antigens from *T. pallidum*, clone pMN23, and clone pMN24, but not with any negative control clones pMN20, pBR322, or pMN7 (FIG. 5). A similar Western blot probed with anti-47 kDa mAb 11E3 gave identical results (not shown). When another blot was probed with mAb 3B5, it revealed the presence of the 34 kDa antigen in *T. pallidum* and clone pMN20, but not in clones pMN23, pMN24, pMN7, or pBR322, as expected (not shown).

Further Western blotting experiments revealed that at least six of seven human secondary syphilitic sera reacted with the recombinant form of the 47 kDa immunogen (1 result was equivocal), while normal human serum did not (not shown). The same human syphilitic sera were unreactive with *E. coli* harboring the cloning vector alone. The experiments confirmed the reactivity of human antibodies elicited in response to the naturally-acquired infection by *T. pallidum* with the recombinant DNA-derived 47 kDa immunogen expressed in *E. coli*.

Evidence is presented for the cloning and expression of the major 47 kDa surface immunogen of *T. pallidum* in *E. coli*. The 5.4 kd DNA insert encoding the 47 kDa immunogen possessed ample coding capacity for the immunogen; approximately 1.3 kb of DNA would be required to encode a mature 47 kDa antigen. A 3.85 kd HindIII DNA fragment subclone of the 5.4 kd total DNA insert was incapable of expressing the relevant epitope(s) when subclones were analyzed using mAbs 11E3 or 8G2. Additional recent preliminary subcloning experiments suggest that the rightward three PstI fragments of clone pMN23 (FIG. 2) are not necessary for expression of the 47 kDa immunogen. Portions of all three of the leftward PstI fragments of pMN23 appear to be required for expression of the 47 kDa gene product, but apparently only a small righthand portion of the left 1,150 bp PstI fragment is required for expression. The 510 bp PstI fragment is required for expression. Deletion of the 510 bp PstI fragment results in a truncated gene product with a molecular mass of about 44.5 kDa (reactive with mAb 11E3). These preliminary results suggest that the direction of transcription is from let to right relative to FIG. 2, that transcription for the structural 47 kDa gene begins just to the left of the ClaI site and proceeds to about 70 base pairs to the right of the second internal PstI site in the cloned insert. Further experiments are necessary for more precise determinations.

On the basis of prior studies (Fehniger et al. (1984) *Infect. Immun.*, V 46, pp 598–607; Hansen et al. (1985), *J. Bacteriol.*, V 162, pp 1227–1237; Norgard et al. (1983) *Infect. Immun.*, V 42, pp 435–445; Stamm et al. (1983) *Infect. Immun.*, V 41, pp 709–721; and Swancutt et al. (1986) *Infect. Immun.*, V 52, pp 110–119), it is likely that *E. coli* is utilizing the *T. pallidum* promoter for transcription of the 47 kDa gene. However, preliminary experiments suggest that the level of expression of the 47 kDa gene product in *E. coli* is approximately $10^{-3}$ to $10^{-4}$ less efficient (on a per cell basis) in comparison with *T. pallidum*. Initial utilization of the expression vector system described by Tabor and Richardson (Tabor et al. (1985) *Proc. Natl. Acad. Sci. USA*, V 82, pp 1074–1078) increased expression of the 47 kDa gene product more than 100-fold (unpublished).

The availability of purified 47 kDa recombinant immunogen produced as described herein now provides an opportunity for direct diagnostic, pathogenesis, and vaccine assessment. That both the native and recombinant DNA-derived forms of the 47 kDa immunogen possess identical electrophoretic mobilities on polyacrylamide gels and that antibodies present in human syphilitic sera bind to the recombinant form of the antigen suggest that the recombinant molecule may be used in place of the native immunogen in these studies.

Expression of the 47 kDa immunogen in *E. coli* will allow more precise biochemical analysis of the 47 kDa protein. Lukehart et al. proposed that the 48 kDa immunogen of *T. pallidum* may be a glycoprotein (Lukehart et al., (1982) *J. Immunol.*, V 129, pp 833–838). Although F-pilin of *E. coli* may be considered a glycoprotein (containing one glucose and possibly one each of galactose and of a dideoxy hexose) (Willetts et al. (1980) *Ann. Rev. Genet.*, V 14, pp 41–76), the precedent for glycoproteins in prokaryotes is poor. The fact that *E. coli* expresses a 47 kDa antigen with an identical electrophoretic mobility to the native 47 kDa immunogen of *T. pallidum* suggests that the 47 kDa immunogen is not a glycoprotein.

The native 47 kDa immunogen often appears as a "47–48 kDa doublet" on Western blots of the immunogen (Marchitto et al. (1984) *Infect. Immun.*, V 45, pp 660–666; and Norgard et al. (1984), *J. Clin. Microbiol.*, V 20, pp 711–717). The appearance of the "doublet" is obscured in RIP analysis (Jones et al., (1984) *J. Exp. Med.*, V 160, pp 1404–1420), presumably due to the intensity of the broad radioactive band appearing on the polyacrylamide gel. Two-dimensional gel analysis of the 47 kDa antigen resolved as a 2-3 spot cluster with similar isoelectric points of about pH 5.5–5.7, possessing the 47–48 kDa doublet appearance in the second dimension (unpublished data). This is consistent with other unpublished two-dimensional gel data obtained independently in the laboratory of S. J. Norris. (S. J. Norris, personal communication). The nature of the cluster of polypeptide spots having similar isoelectric points in unclear, but the "doublet" phenomenon remains consistent with single-dimensional gel analysis. The 48 kDa component of the 47–48 kDa doublet always appears as a minor band. The 48 kDa component may represent unprocessed outer membrane protein precursor which is subsequently cleaved to the lower molecular weight (mature) 47 kDa form during transmembrane secretion. Alternatively, the 48 kDa component may represent some post-translational modification of the 47 kDa product. The recombinant DNA-derived 47 kDa immunogen has not yet been observed to exhibit the 47–48 kDa doublet phenomenon, although this may be due to undetectably low levels of 48 kDa product expressed in *E. coli*. Subcloning of the 47 kDa gene into an expression vector (Tabor et al. (1985) *Proc. Natl. Acad. Sci. USA*, V 82, pp 1074–1078) should help to clarify the observation. DNA sequencing studies also will be instrumental in establishing the primary amino acid sequence of a mature 47 kDa immunogen and any possible precursor form.

The cloning and expression of the 47 kDa immunogen of *T. pallidum* in *E. coli* provides tools to help assess the chemical composition of the protein and the structure-function relationship of the native 47 kDa immunogen in *T. pallidum*, possibly leading to an increased understanding of the biology of this elusive pathogen. DNA encoding the 47 kDa antigen may be useful as a diagnostic DNA probe (Moseley et al. (1980) *J. Infect. Dis.*, V 142, pp 892–898) to identify treponemal pathogens in gential ulcers, skin lesions, and other body fluids. Purified 47 kDa immunogen can be used to reexamine, using in vitro and in vivo methods, both humoral and cell-mediated immune responses to purified antiens; this may help to further clarify the respective roles of both arms of the immune response to *T. pallidum* infection in the host. The recombinant DNA-derived immunogen also may provide the basis for an improved serological test for syphilis, potentially possessing increased specificity and simplicity over currently employed methods. Additionally, recombinant immunogen should allow direct assessment of the immunogenic potential of the 47 kDa immunogen. Inasmuch as the 47 kDa immunogen has, at the very least, pathogen-specific epitopes, the demonstration of vaccinogenic potential for the recombinant molecule may be extended to a broad spectrum treponemal vaccine.

Changes may be made in the components such as vectors, plasmids, *T. pallidum* DNA inserts or host microorganisms described herein or in the steps or the sequence of steps of the methods described herein without departing from the concept and scope of the invention as defined in the following claims.

What is claimed is:

1. A recombinant plasmid adapted for transformation of a microbial host, said plasmid comprising a plasmid vector into which a DNA segment which codes for the 47 kDa surface immunogen of *Treponema pallidum* has been inserted.

2. A transformant microorganism which includes a recombinant plasmid, said plasmid comprising a plasmid vector into which a DNA segment encoding the 47 kDa surface immunogen of *Treponema pallidum* has been inserted.

3. A microorganism of the strain *Escherichia coli* having the identifying characteristics of ATCC No. 67204, said microorganism being capable of producing the 47 kDa surface immunogen of *Treponema pallidum* reactive with antibodies to *Treponema pallidum*.

4. The recombinant plasmid of claim 1 defined further as being plasmid pMN23 having the characteristics of ATCC Deposit No. 67204.

* * * * *